(12) United States Patent
Nagasawa et al.

(10) Patent No.: US 11,806,257 B2
(45) Date of Patent: Nov. 7, 2023

(54) DRUG-ELUTING STENT INCLUDING CRYSTALLINE CILOSTAZOL

(71) Applicant: OTSUKA MEDICAL DEVICES CO., LTD, Tokyo (JP)

(72) Inventors: Masakazu Nagasawa, Tokyo (JP); Hiroshi Ohno, Tokyo (JP); Takafumi Ohyama, Tokyo (JP)

(73) Assignee: OTSUKA MEDICAL DEVICES CO., LTD., Tokyo (JP)

( * ) Notice: Subject to any disclaimer, the term of this patent is extended or adjusted under 35 U.S.C. 154(b) by 0 days.

(21) Appl. No.: 17/597,449

(22) PCT Filed: Jul. 8, 2020

(86) PCT No.: PCT/JP2020/026688
§ 371 (c)(1),
(2) Date: Jan. 6, 2022

(87) PCT Pub. No.: WO2021/006291
PCT Pub. Date: Jan. 14, 2021

(65) Prior Publication Data
US 2022/0160525 A1 May 26, 2022

(30) Foreign Application Priority Data

Jul. 9, 2019 (JP) ................................. 2019-127529

(51) Int. Cl.
*A61F 2/82* (2013.01)
*A61K 31/4709* (2006.01)
(Continued)

(52) U.S. Cl.
CPC ............ *A61F 2/82* (2013.01); *A61K 31/4709* (2013.01); *A61L 31/02* (2013.01); *A61L 31/06* (2013.01);
(Continued)

(58) Field of Classification Search
CPC ...... A61F 2/28; A61F 2/86; A61F 2/82; A61L 31/08; A61L 31/12; A61L 31/16; A61L 2300/63
See application file for complete search history.

(56) References Cited

U.S. PATENT DOCUMENTS

| 5,824,048 A | 10/1998 | Tuch |
| 2005/0010282 A1 | 1/2005 | Thornton et al. |

(Continued)

FOREIGN PATENT DOCUMENTS

| CN | 1465410 A | 1/2004 |
| CN | 101052362 A | 10/2007 |

(Continued)

OTHER PUBLICATIONS

Machine Translation of Office Action dated May 25, 2022 in Taiwanese Application No. 109123057.
(Continued)

*Primary Examiner* — Carlos A Azpuru
(74) *Attorney, Agent, or Firm* — Sughrue Mion, PLLC (57) ABSTRACT

Provided is a stent comprising: a stent skeleton; and a deposition layer containing a plurality of layers deposited on the stent skeleton; each layer of the deposition layer comprising crystalline cilostazol, at least one of the plurality of layers comprising a bioabsorbable polymer, wherein elution of not more than 5% by mass of the crystalline cilostazol occurs by 24 hours after the stent is brought into contact in vitro at 37° C. with an elution medium of a phosphate-buffered sodium chloride solution containing 0.25% by mass of sodium lauryl sulfate.

20 Claims, 1 Drawing Sheet (51) Int. Cl.
- *A61L 31/02* (2006.01)
- *A61L 31/06* (2006.01)
- *A61L 31/08* (2006.01)
- *A61L 31/12* (2006.01)
- *A61L 31/16* (2006.01)

(52) U.S. Cl.
CPC .............. *A61L 31/08* (2013.01); *A61L 31/12* (2013.01); *A61L 31/16* (2013.01)

(56) References Cited

U.S. PATENT DOCUMENTS

| | | |
|---|---|---|
| 2005/0033414 A1 | 2/2005 | Zhang et al. |
| 2005/0043788 A1 | 2/2005 | Luo et al. |
| 2006/0161242 A1 | 7/2006 | Lee et al. |
| 2007/0250157 A1 | 10/2007 | Nishide et al. |
| 2008/0071359 A1 | 3/2008 | Thornton et al. |
| 2010/0076544 A1 | 3/2010 | Hoffmann et al. |
| 2010/0198344 A1 | 8/2010 | Omura et al. |
| 2010/0241220 A1 | 9/2010 | McClain et al. |
| 2010/0249914 A1 | 9/2010 | Omura et al. |
| 2010/0280600 A1 | 11/2010 | Dave et al. |
| 2012/0130481 A1 | 5/2012 | Falotico et al. |
| 2012/0310329 A1 | 12/2012 | Omura et al. |
| 2013/0018455 A1 | 1/2013 | Omura et al. |
| 2013/0115363 A1 | 5/2013 | Omura et al. |
| 2014/0121747 A1 | 5/2014 | Clerc et al. |
| 2016/0175127 A1 | 6/2016 | Ito |
| 2017/0319362 A1 | 11/2017 | Manabe |
| 2017/0333231 A1 | 11/2017 | Li |
| 2022/0008231 A1 | 1/2022 | Clerc et al. |

FOREIGN PATENT DOCUMENTS

| | | | |
|---|---|---|---|
| CN | 101641059 | * | 10/2011 |
| CN | 101641059 B | | 10/2011 |
| CN | 103948458 A | | 7/2014 |
| CN | 203829101 U | | 9/2014 |
| CN | 204542477 U | | 8/2015 |
| CN | 107106309 A | | 8/2017 |
| JP | 2005-531391 | * | 10/2005 |
| JP | 2005-531391 A | * | 10/2005 |
| JP | 2005-531391 A1 | * | 10/2005 |
| JP | 2006-198390 A | | 8/2006 |
| JP | 2007-528753 A | | 10/2007 |
| JP | 2010516414 A | | 5/2010 |
| JP | 2012-196252 A | | 10/2012 |
| JP | 2013-126558 A | | 6/2013 |
| JP | 2014-502193 A | | 1/2014 |
| JP | 2015-515358 A | | 5/2015 |
| WO | 2005016187 A1 | | 2/2005 |
| WO | 201/198390 | * | 8/2006 |
| WO | 2012/067913 A1 | | 5/2012 |
| WO | 2014065941 A1 | | 5/2014 |
| WO | 2010/02139 A1 | * | 2/2015 |
| WO | 2015/020139 A1 | * | 2/2015 |
| WO | 2016/067994 A1 | * | 2/2016 |
| WO | 2016/067994 A1 | | 5/2016 |

OTHER PUBLICATIONS

English Translation of Office Action dated Jun. 1, 2022 in Mexican Application No. MX/a/2021/00389.

Parker et al., "Control of cilostazol release kinetics and direction from a stent using a reservoir-based design", Journal of Biomedical Materials Research Part B: Applied Biomaterials, 2012, vol. 100B, pp. 603-610 (8 pages total).

International Search Report of PCT/JP2020/026688 dated Aug. 18, 2020. [PCT/ISA/210].

International Preliminary Report on Patentability issued by the International Searching Authority in counterpart Application No. PCT/JP2020/026688.

Miaozhang Zhu et al, "Fundamentals and Clinics of Cardiovascular Physiology", Higher Education Press, Jan. 2011, p. 447 (3 pages total).

Office Action dated Nov. 25, 2022 in Chinese Application No. 202080048831.X.

Doo-Soo Jeon et al., "The Effect of Cilostazol on Stent Thrombosis After Drug-Eluting Stent Implantation", The Korean Society of Cardiology, 2010, pp. 10-15 (6 pages total).

Extended European Search Report dated May 30, 2023 in European Application No. 20837247.4.

* cited by examiner

DRUG-ELUTING STENT INCLUDING CRYSTALLINE CILOSTAZOL

CROSS REFERENCE TO RELATED APPLICATIONS

This application is a National Stage of International Application No. PCT/JP2020/026688 filed Jul. 8, 2020, claiming priority based on Japanese Patent Application No. 2019-127529 filed Jul. 9, 2019.

TECHNICAL FIELD

The present invention relates to a stent coated with cilostazol, and a method of producing it, more specifically, to a stent having a plurality of layers containing cilostazol, and a method of producing it.

BACKGROUND ART

In recent years, arteriosclerotic diseases such as myocardial infarction, angina pectoris, apoplectic stroke, and peripheral vascular diseases are increasing. As a secure therapeutic method for arteriosclerotic diseases, for example, percutaneous transluminal angioplasty (hereinafter simply referred to as "PTA") such as percutaneous transluminal coronary angioplasty in a coronary artery of the heart, wherein a stenotic portion or an occluded portion of a blood vessel is surgically expanded, is widely used. In PTA, a treatment method that is carried out for a stenotic portion or an occluded portion of a coronary artery is specifically called percutaneous transluminal coronary angioplasty (hereinafter simply referred to as "PTCA").

PTCA is a technique in which a thin tube having a balloon attached to its tip (balloon catheter), or a stent, is inserted from an artery of an arm or a femoral region into a stenotic portion of a heart coronary artery, and the balloon at the tip is inflated to expand the stenotic blood vessel, to thereby recover the blood flow. By this, the intravascular space of the lesion site is expanded to increase the blood that flows through the intravascular space. PTCA is used not only for treatment of arteriosclerotic diseases, but also for, for example, treatment of stenosis of a shunt blood vessel formed in an arm of a hemodialysis patient.

In general, a blood vessel portion subjected to PTCA is damaged due to detachment of endothelial cells, damaging of the elastic lamina, or the like, and this causes the proliferation of the intima as a healing response of the blood vessel wall. As a result, about 30 to 40% of the cases with successful expansion of a stenotic lesion by PTCA suffer from restenosis.

The restenosis in humans is thought to be caused, mainly, by the inflammatory process found as adhesion and/or infiltration of monocytes which occurs one to three days after PTCA, and by the intimal thickening/formation process by smooth muscle cells, whose proliferation reaches the peak about 45 days later. In cases where the restenosis occurs, PTCA needs to be carried out again. Therefore, establishment of a method of prevention, and a method of treatment, of the restenosis is an urgent task.

In view of this, attempts have been intensively made in order to reduce the restenosis rate by using a drug-eluting medical device (stent) to be placed in a lumen, the device having an anticancer drug, an immunosuppressive drug, an anti-inflammatory drug, or a proliferation inhibitor for smooth muscle cells supported on a surface of the stent or the like, which deice allows topical release of the drug for about several days at the site of placement in the lumen.

The drugs applied to drug-eluting stents are commonly limus drugs that can act as an anticancer drug or an immunosuppressive drug. With their strong cytotoxicities, these drugs strongly suppress the proliferation of vascular smooth muscle cells, that is, the intimal thickening, which is the main cause of the restenosis. However, since they also strongly suppress regeneration of vascular endothelial cells, they may induce delayed in-stent thrombosis, which is clinically very problematic.

Attempts to use drugs other than limus drugs have also been made. Examples of such drugs include cilostazol, which is noncytotoxic, but whose preparation is assumed to be difficult because of its poor solubility in water. For example, Patent Document 1 proposes a drug-eluting stent comprising a mixture containing a bioabsorbable polymer having a molecular weight of 40,000 to 600,000 and cilostazol, wherein a surface of a stent body composed of a metal or a polymer material is coated with the mixture (see, for example, claims and [0015]). Patent Document 1 also discloses that the stent allows elution of the drug during the period of occurrence of restenosis in the inflammatory process or the intimal thickening/formation process after the placement of the stent, wherein the drug acts on intravascular cells to effectively suppress intimal thickening, so that restenosis after placement of a stent, which has hitherto frequently occurred, can be remarkably improved (see [0028]).

PRIOR ART DOCUMENT

Patent Document

[Patent Document 1] WO 2016/067994

SUMMARY OF THE INVENTION

Problems to be Solved by the Invention

The stent disclosed in Patent Document 1 is used for, for example, a relatively thick artery such as a heart coronary artery, and required to act on the inflammatory process found as adhesion and/or infiltration of monocytes which occurs one to three days after PTCA. Thus, the stent according to Patent Document 1 is required to produce the effect by allowing release of cilostazol for several days after the placement.

On the other hand, in recent years, peripheral artery diseases (PADs) caused by infarction or the like of peripheral arteries, which are thinner, are attracting attention. For example, there are diseases in which arteriosclerosis occurs in leg blood vessels to cause thinning or clogging of the blood vessels, leading to insufficiency of blood flow to the legs. They cause symptoms such as numbness, pain, and cold feeling during walking. As the disease progresses, the patient becomes unable to walk (intermittent claudication), or feels pain in the legs even at rest. Further progression of the disease may lead to ulceration or necrosis of the legs, and, in severe cases, surgery is required for the legs.

Even in cases where PAD merely exhibits symptoms of the limbs, arteriosclerosis may affect not only the limbs, but also blood vessels in the whole body. In cases where PAD is left untreated, it may also cause myocardial infarction, angina pectoris, cerebral infarction, and/or the like. Various therapeutic methods such as pharmacotherapy, physical therapy, and surgery are available for PAD depending on the progression of the disease state and the therapeutic goal. By realizing a drug-placing stent for peripheral arteries, a novel therapeutic method for minimally invasive treatment of PAD can be provided.

As a result of studies, the present inventors considered that a stent that allows the presence of an effective component in an arterial vessel in a diseased state, for a longer period (for example, 6 to 12 months) than a drug-placing stent for a heart coronary artery (for example, Patent Document 1) is required.

An object of the present invention is to provide a drug-placing stent that allows the presence of an effective component in a blood vessel in a diseased state, for a longer period (for example, 6 to 12 months). Such a drug-placing stent can be suitably used for treatment of a peripheral blood vessel (for example, peripheral arterial blood vessel), and can provide a minimally invasive therapeutic method.

Means for Solving Problems

As a result of intensive study, the present inventors discovered that a drug-placing stent comprising: a stent skeleton; and a deposition layer containing a plurality of layers deposited on the stent skeleton; each layer of the deposition layer comprising crystalline cilostazol, at least one of the plurality of layers comprising a bioabsorbable polymer, wherein elution of not more than 5% by mass of the crystalline cilostazol occurs by 24 hours in a test on the elution rate in vitro, can be obtained. The present inventors also discovered that such a drug-placing stent can be suitably used for peripheral blood vessels, thereby completing the present invention.

The present description includes the following embodiments.

1. A stent comprising:
   a stent skeleton; and
   a deposition layer containing a plurality of layers deposited on the stent skeleton;
   each layer of the deposition layer comprising crystalline cilostazol (CLZ),
   at least one of the plurality of layers comprising a bioabsorbable polymer,
   wherein elution of not more than 5% by mass of the crystalline cilostazol occurs by 24 hours after the stent is brought into contact in vitro with an elution medium, at 37° C., of a phosphate-buffered sodium chloride solution containing 0.25% by mass of sodium lauryl sulfate.
2. A stent comprising:
   a stent skeleton; and
   a deposition layer containing a plurality of layers deposited on the stent skeleton;
   each layer of the deposition layer comprising crystalline cilostazol (CLZ),
   at least one of the plurality of layers comprising a bioabsorbable polymer,
   wherein elution of not more than 20% by mass of the crystalline cilostazol occurs by 15 days after the stent is brought into contact in vitro at 37° C. with an elution medium of a phosphate-buffered sodium chloride solution containing 0.25% by mass of sodium lauryl sulfate.
3. The stent according to 1 or 2, wherein the deposition layer has at least two layers, and wherein the content of cilostazol in a first layer, which is closer to the stent, is higher than the content of cilostazol in a second layer, which is more distant from the stent.
4. The stent according to any one of 1 to 3, wherein
   the deposition layer has at least two layers;
   the content of cilostazol in the first layer, which is closer to the stent, is higher than the content of cilostazol in the second layer, which is more distant from the stent; and
   both layers comprise a bioabsorbable polymer.
5. The stent according to any one of 1 to 4, wherein the bioabsorbable polymer comprises not less than 90% by mass of polylactic acid.
6. The stent according to any one of 1 to 5, wherein the bioabsorbable polymer comprises L-lactide and DL-lactide at a mass ratio of 6:4 to 8:2, and has a viscosity of 1.8 to 4.5 dL/g.
7. The stent according to any one of 1 to 5, wherein the bioabsorbable polymer comprises not less than 90% by mass of L-lactide, and has a viscosity of 0.6 to 1.4 dL/q.
8. The stent according to any one of 1 to 7, to be used for a peripheral blood vessel.
9. A stent comprising:
   a stent skeleton;
   a first layer deposited on the stent skeleton; and
   a second layer deposited on the first layer;
   the first layer and the second layer each comprising cilostazol and a bioabsorbable polymer,
   the bioabsorbable polymer comprising L-lactide and DL-lactide at a mass ratio of 6:4 to 8:2, and having a viscosity of 1.8 to 4.5 dL/g,
   the first layer comprising 470±47 μg of cilostazol and 313±31 μg of the bioabsorbable polymer,
   the second layer comprising 30±3 μg of cilostazol and 270±27 μg of the bioabsorbable polymer.

Effects of the Invention

A drug-placing stent of an embodiment of the present invention is capable of allowing elution of not more than 5% by mass of the crystalline cilostazol by 24 hours in a test on the elution rate in vitro. Thus, the drug-placing stent of the embodiment of the present invention is capable of allowing elution of crystalline cilostazol for a longer period, and can be more suitably used for peripheral blood vessels.

EMBODIMENT FOR CARRYING OUT THE INVENTION

A stent of one embodiment of the present invention comprises:
a stent skeleton; and
a deposition layer containing a plurality of layers deposited on the stent skeleton;
each layer of the deposition layer comprising crystalline cilostazol,
at least one of the plurality of layers comprising a bioabsorbable polymer,
wherein
elution of not more than 5% by mass of the crystalline cilostazol occurs by 24 hours after the stent is brought into contact in vitro with an elution medium, at 37° C., of a phosphate-buffered sodium chloride solution containing 0.25% by mass of sodium lauryl sulfate.

A stent of another embodiment of the present invention comprises:
a stent skeleton; and
a deposition layer containing a plurality of layers deposited on the stent skeleton;
each layer of the deposition layer comprising crystalline cilostazol,
at least one of the plurality of layers comprising a bioabsorbable polymer,
wherein elution of not more than 20% by mass of the crystalline cilostazol occurs by 15 days after the stent is brought into contact in vitro at 37° C. with an elution medium of a phosphate-buffered sodium chloride solution containing 0.25% by mass of sodium lauryl sulfate.

A stent of still another embodiment of the present invention comprises:
a stent skeleton;
a first layer deposited on the stent skeleton; and
a second layer deposited on the first layer;
the first layer and the second layer each comprising cilostazol and a bioabsorbable polymer,
the bioabsorbable polymer comprising L-lactide and DL-lactide at a mass ratio of 6:4 to 8:2, and having a viscosity of 1.8 to 4.5 dL/g,
the first layer comprising 470±47 μg of cilostazol and 313±31 μg of the bioabsorbable polymer,
the second layer comprising 30±3 μg of cilostazol and 270±27 μg of the bioabsorbable polymer.

A stent of an embodiment of the present invention comprises: a stent skeleton; and a deposition layer containing a plurality of layers deposited on the stent skeleton.

In an embodiment of the present invention, "stent skeleton" means a skeleton forming a stent, and is usually not limited as long as, for example, it is formed as a coarse-mesh cylinder using a metal or a polymer material, and as long as a desired stent of the present invention can be obtained therewith.

Examples of the stent skeleton made of a metal include stent skeletons made of nickel, cobalt, chromium, titanium, or an appropriate alloy such as stainless steel. The stent skeleton is preferably a stent skeleton made of a metal comprising a cobalt-chromium alloy as a major component.

A stent of an embodiment of the present invention comprises a deposition layer containing a plurality of layers deposited on the stent skeleton. Each layer of the deposition layer comprises crystalline cilostazol, and at least one of the plurality of layers comprises a bioabsorbable polymer.

In the present description, "cilostazol" has the chemical name 6-[4-(1-cyclohexyl-1H-tetrazol-5-yl)butoxy]-3,4-dihydrocarbostyryl. Cilostazol has platelet aggregation inhibition action, phosphodiesterase (PDE) inhibition action, antiulcer action, hypotensive action, and anti-inflammatory action, and is known to be useful as an antithrombotic drug, a cerebral circulation improver, an antiphlogistic, an antiulcer drug, an antihypertensive drug, an antiasthmatic drug, a phosphodiesterase inhibitor, and the like. The cilostazol is not limited as long as a desired stent of the present invention can be obtained therewith. The cilostazol also includes pharmaceutically acceptable salts thereof.

The cilostazol is preferably crystalline. The cilostazol preferably has a crystal structure rather than having no crystal structure (rather than being amorphous), from the viewpoint of reducing the elution rate.

In an embodiment of the present invention, the bioabsorbable polymer is not limited as long as a desired stent of the present invention can be obtained therewith. Examples of the bioabsorbable polymer include polylactic acid including lactide, and its molecular weight (Mw: weight average molecular weight) may be 40,000 to 700,000. Its viscosity may be 0.4 to 5.0 dL/g, or may be 0.4 to 4.2 dL/g. Further, the bioabsorbable polymer may comprise DL-lactide, L-lactide, or the like, and may comprise glycolide, caprolactone, or the like. Specific examples of the bioabsorbable polymer include: polymers containing DL-lactide having a molecular weight of 10,000 to 1,000,000; polymers containing L-lactide and DL-lactide at a mass ratio of 6:4 to 8:2, and having a molecular weight of 300,000 to 650,000 or a viscosity of 1.8 to 4.5 dL/g; and polymers having a molecular weight of 50,000 to 150,000 or containing not less than 90% by mass L-lactide, and having a viscosity of 0.6 to 1.4 dL/g (including poly(L-lactic acid) containing 100% by mass L-lactide). As the bioabsorbable polymer, a commercially available product may be used. Examples of the commercially available product include LR704S (trade name), L206S (trade name), and LR706S (trade name). The bioabsorbable polymers may be used either individually or in combination.

The bioabsorbable polymer preferably comprises not less than 90% by mass, more preferably comprises not less than 93% by mass, still more preferably comprises 96% by mass polylactic acid. In cases where the bioabsorbable polymer comprises not less than 90% by mass polylactic acid, the polymer is capable of sustained release, which is an advantageous effect.

The deposition layer has at least two layers, wherein the content of cilostazol in a first layer, which is closer to the stent skeleton, is preferably higher than the content of cilostazol in a second layer, which is more distant from the stent skeleton. In cases where the layer closer to the stent skeleton has a higher content of cilostazol, the layer allows sustained release for a long period, which is an advantageous effect.

The content of cilostazol in the first layer is preferably 300 to 750 μg, more preferably 350 to 550 μg, still more preferably 440 to 480 μg. Further, the first layer preferably comprises 470±47 μg cilostazol.

The content of cilostazol in the second layer is preferably 0 to 100 μg, more preferably 10 to 80 μg, still more preferably 20 to 60 μg. Further, the second layer preferably comprises 30±3 μg cilostazol.

The content of cilostazol in the first layer is preferably 40 to 100% by mass, more preferably 50 to 70% by mass, still more preferably 55 to 65% by mass.

The content of cilostazol in the second layer is preferably 0 to 50% by mass, more preferably 2 to 20% by mass, still more preferably 5 to 10% by mass.

The deposition layer has at least two layers, wherein the content of cilostazol in a first layer, which is closer to the stent, is preferably higher than the content of cilostazol in a second layer, which is more distant from the stent, and wherein both layers preferably comprise a bioabsorbable polymer.

The content of the bioabsorbable polymer in the first layer is preferably 0 to 500 μg, more preferably 250 to 350 μg, still more preferably 300 to 320 μg. Further, the first layer preferably comprises 313±31 μg of the bioabsorbable polymer.

The content of the bioabsorbable polymer in the second layer is preferably 180 to 540 μg, more preferably 200 to 300 μg, still more preferably 260 to 285 μg. Further, the second layer preferably comprises 270±27 μg of the bioabsorbable polymer.

The content of the bioabsorbable polymer in the first layer is preferably 0 to 60% by mass, more preferably 25 to 50% by mass, still more preferably 35 to 45% by mass.

The content of the bioabsorbable polymer in the second layer is preferably not less than 70% by mass, more preferably not less than 80% by mass, still more preferably not less than 90% by mass.

In a stent of an embodiment of the present invention, elution of not more than 3% by mass of the crystalline cilostazol occurs by 24 hours after the stent is brought into contact in vitro with an elution medium, at 37° C., of a phosphate-buffered sodium chloride solution containing 0.25% by mass sodium lauryl sulfate.

In a stent of an embodiment of the present invention, elution of not more than 20% by mass of the crystalline cilostazol preferably occurs by 15 days after the stent is brought into contact; elution of not more than 7% by mass of the crystalline cilostazol preferably occurs by 8 days after the stent is brought into contact; and elution of not more than 5% by mass, more preferably not more than 3% by mass, of the crystalline cilostazol preferably occurs by 1 day after the stent is brought into contact; in vitro at 37° C. with an elution medium of a phosphate-buffered sodium chloride solution containing 0.25% by mass sodium lauryl sulfate.

In a stent of an embodiment of the present invention, elution of, for example, not less than 1.0% by mass of the crystalline cilostazol may occur, or not less than 0.1% by mass of the crystalline cilostazol may occur, by 15 days after the stent is brought into contact; elution of, for example, not less than 0.5% by mass of the crystalline cilostazol may occur, or not less than 0.05% by mass of the crystalline cilostazol may occur, by 8 days after the stent is brought into contact; elution of, for example, not less than 0.1% by mass of the crystalline cilostazol may occur, or not less than 0.01% by mass of the crystalline cilostazol may occur, by 1 day after the stent is brought into contact; in vitro at 37° C. with an elution medium of a phosphate-buffered sodium chloride solution containing 0.25% by mass sodium lauryl sulfate.

In cases where elution of not more than the above-described ratio of the crystalline cilostazol occurs by the above-described time after the stent is brought into contact in vitro with an elution medium, at 37° C., of a phosphate-buffered sodium chloride solution containing 0.25% by mass sodium lauryl sulfate, the cilostazol can be released for more than three months, so that the crystalline cilostazol can be allowed to be present in the living body for a very long time.

Thus, a stent of an embodiment of the present invention can be suitably used, for example, for a peripheral blood vessel, preferably for a peripheral arterial blood vessel.

Further, a stent of an embodiment of the present invention can also be used for, for example, relatively thick arteries for which stents have conventionally been used, such as heart coronary arteries and lower extremity arteries.

As long as a desired stent of the present invention can be obtained, the method of producing a stent of an embodiment of the present invention is not limited.

A stent of an embodiment of the present invention can be produced using, for example, a production method comprising: (i) providing a stent skeleton; (ii) providing a mixture containing cilostazol; (iii) coating the stent skeleton with the mixture; and repeating (ii) and (iii) (wherein the content of cilostazol, and/or the like is/are adjusted).

The mixture containing cilostazol may contain the bioabsorbable polymer described above, in addition to the cilostazol. The mixture may also contain a solvent such as an additive. Since cilostazol is poorly soluble, the bioabsorbable polymer is required to prevent detachment of the coating, and to maintain high strength.

The mixing mass ratio between the cilostazol and the bioabsorbable polymer such as polylactic acid is preferably 1:0.5 to 1:1.5. In cases where the ratio is within this range, a better intimal-thickening effect can be obtained. In cases where the mixing mass ratio is 1:1.1 to 1:1.5, the coating strength and the sustained-release effect can be further increased.

In an embodiment of the present invention, the method of coating the stent skeleton with the mixture of cilostazol and the bioabsorbable polymer is not limited as long as a desired stent of the present invention can be obtained. For example, a simple spraying method, a dipping method, an electrode-position method, an ultrasonic spray method, or the like that has been conventionally used may be employed. From the viewpoint of coating, it is preferred to use an ultrasonic spray method.

The embodiments described above may be combined as appropriate when it is possible.

Embodiments of the present invention are described below in detail with reference to drawings.

Figure 1:
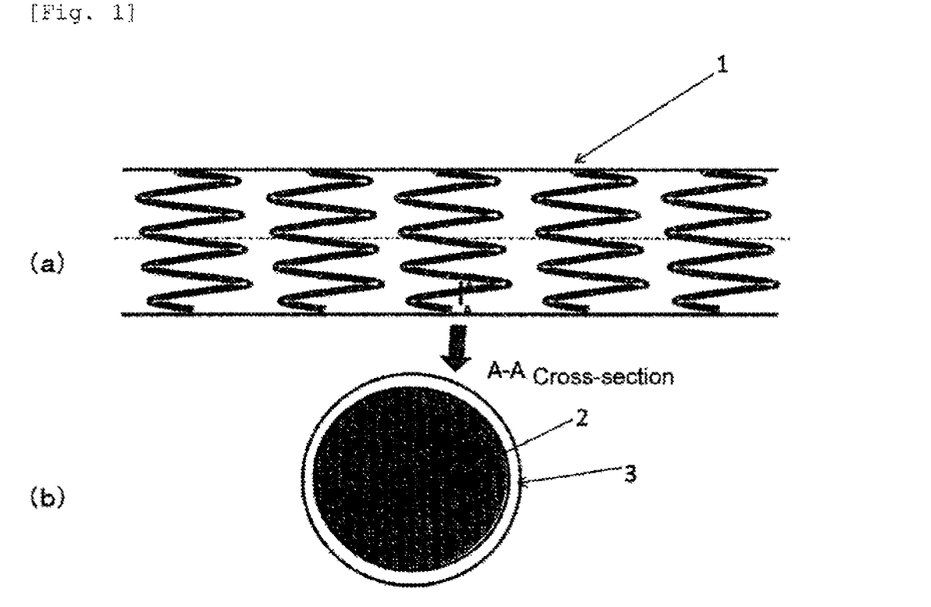
FIG. 1 schematically illustrates the whole shape (a) of a stent of an embodiment of the present invention, and a cross-section (b) of the stent along A-A.

FIG. 1(a) schematically illustrates a drug-eluting stent 1 of one embodiment of the present invention. The drug-eluting stent 1 has a cylindrical shape having a longitudinal axis, and a lumen is formed therein. In the drug-eluting stent 1, the cylindrical shape has a coarse-mesh-like side such that it is laterally expandable. Usually, the net may be formed with a member 2 (a wire of a metal or a polymer material) forming the stent skeleton. The drug-eluting stent 1 is usually inserted in an unexpanded form into the body. It is expanded at a treatment site in a blood vessel, and placed in the blood vessel. The expansion may be achieved by a balloon catheter in the blood vessel. FIG. 1(a) schematically illustrates the net. As long as a desired stent of the present invention can be obtained, the pattern of the net is not limited.

FIG. 1(b) schematically illustrates a cross-section (A-A cross-section) of a wire forming the stent skeleton in FIG. 1(a).

In a drug-eluting stent 1 of one embodiment of the present invention, a deposition layer 3 is formed on the stent skeleton member 2. The stent skeleton member 2 may be prepared using an arbitrary method. For example, it may be prepared by laser, electric discharge milling, chemical etching, or another means, from a hollow or formed stainless-steel tube. The stent skeleton member 2 may be formed with nickel, cobalt, chromium, titanium, or an appropriate alloy of stainless steel etc.

The deposition layer 3 is formed with at least two layers. In FIG. 1(b), the plurality of layers are not illustrated.

Figure 2:
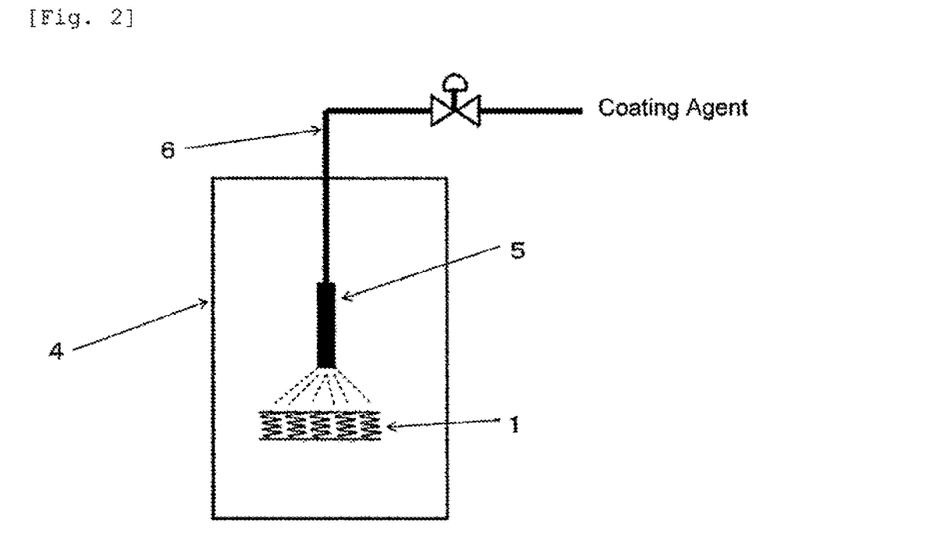
FIG. 2 schematically illustrates an embodiment of coating of a stent with a coating agent using an ultrasonic atomizer.

FIG. 2 schematically illustrates an ultrasonic spray coating device 4 for forming the deposition layer 3 by application on the stent skeleton member 2. Before the coating step, first, the surface of the stent skeleton member 2 is preferably subjected to plasma treatment using a plasma treatment apparatus (not shown). Thereafter, the stent skeleton member 2 is mounted on a mandrel, followed by attachment to the ultrasonic spray coating device 4. In the ultrasonic spray coating device 4, a coating liquid is transferred by a syringe pump through a pipe 6, and then atomized and sprayed by an ultrasonic spray nozzle 5. During the spray, the stent skeleton member 2 is linearly moved while rotating the member under the ultrasonic nozzle 5, to allow deposition of the deposition layer 3 on the stent skeleton member 2. Thereafter, while rotating and linearly moving the stent skeleton member 2, it is dried under nitrogen gas flow, followed by further drying it in a desiccator under reduced pressure. By this, a drug-eluting stent 1 can be prepared. Depending on the number of layers to be included in the deposition layer 3, different coating liquids are used to coat the stent skeleton member a plurality of times to form the deposition layer 3.

Each coating liquid is provided using a mixture prepared by dissolving cilostazol and a bioabsorbable polymer in a solvent at a ratio in accordance with the deposition layer 3 to be formed. Since the deposition layer 3 includes a plurality of layers, a plurality of coating liquids need to be provided. As the coating solvent, a volatile solvent having a low boiling point may be used for enabling simple removal after coating. Examples of the volatile solvent include methanol, ethanol, trifluoroethanol, hexafluoroisopropanol, isoamyl alcohol, methyl acetate, ethyl acetate, acetone, methyl ethyl ketone, methylene chloride, chloroform, and dichloroethane; and mixed solvents containing at least two of these.

EXAMPLES

The present invention is described below more concretely in more detail by way of Examples and Comparative Examples. However, these Examples are merely embodiments of the present invention, and the present invention is not limited by these examples at all.

The polymers used in the present Examples are shown below in Table 1.

TABLE 1

| Polymer | Viscosity (dL/g) | Molecular weight (Mw: weight average molecular weight) | Composition L: L-lactide DL: DL-lactide G: glycoside C: caprolactine |
|---|---|---|---|
| (a) L206S | 0.8-1.2 | 102,000 | L = 100 |
| (b) LR704S | 2.0-2.8 | >350,000 | L:DL = 70:30 |
| (c) LR706S | 3.3-4.2 | >630,000 | L:DL = 70:30 |
| (d) RG755S | 0.50-0.70 | 63,000 | DL:G = 75:25 |
| (e) RG858S | 1.3-1.7 | 220,000 | DL:G = 85:15 |
| (f) LC703S | 1.3-1.8 | 257,000 | L:C = 70:30 |

The viscosity of each polymer described above means the limiting viscosity (ηη) (dL/g), which was measured by the capillary viscometer method. A sample solution with a concentration of C (g/dL) was provided, and the measured values of the flow time of the sample solution (t) and the flow time of the solvent (t0) were used to calculate the limiting viscosity according to the following equation.

$$[\eta] = \lim_{C \to 0} \frac{\ln \frac{t}{t_0}}{c}$$

An Ubbelohde viscometer was used as the apparatus, and chloroform (25° C.) was used as the solvent.

Further, the weight average molecular weight (Mw) was determined using the Mark-Kuhn-Houwink equation (Mark-Howink-Sakurada equation).

EXAMPLE 1

A cobalt-chromium alloy was used as the stent skeleton member 2. Cilostazol (CLZ) was dissolved in methylene chloride to provide a solution. By ultrasonic spray coating, this solution was applied to the base material cobalt-chromium alloy, to form a first layer composed of 440 µg of cilostazol.

Subsequently, cilostazol and polymer (a) were mixed together at 1:9 (mass ratio), and dissolved in methylene chloride, to provide a solution. By ultrasonic spray coating, this solution was applied to the first layer, to form a second layer composed of 540 µg of polymer (a) and 60 µg of cilostazol, to obtain a stent of Example 1.

EXAMPLES 2 AND 3

Stents of Examples 2 and 3 were produced using the same method as the method described in Example 1 except that polymer (b) or polymer (c) was used instead of polymer (a).

COMPARATIVE EXAMPLES 1 TO 3

Stents of Comparative Examples 1 to 3 were produced using the same method as the method described in Example 1 except that polymers (d) to (f) were used instead of polymer (a).

EXAMPLE 4

A cobalt-chromium alloy was used as the stent skeleton member 2. Cilostazol and polymer (b) were mixed together at a ratio of 3:2, and dissolved in methylene chloride, to provide a solution. By ultrasonic spray coating, this solution was applied to the cobalt-chromium alloy of the stent skeleton member, to form a first layer composed of 313 µg of polymer (b) and 470 µg of cilostazol.

Subsequently, cilostazol and polymer (b) were mixed together at a ratio of 1:9 (mass ratio), and dissolved in methylene chloride, to provide a solution. By ultrasonic spray coating, this solution was applied to the first layer, to form a second layer composed of 270 µg of polymer (b) and 30 µg of cilostazol, to obtain a stent of Example 4.

EXAMPLE 5

A cobalt-chromium alloy was used as the stent skeleton member 2. Cilostazol and polymer (b) were mixed together at a ratio of 3:2, and dissolved in methylene chloride, to provide a solution. By ultrasonic spray coating, this solution was applied to the base material cobalt-chromium alloy, to form a first layer composed of 323 µg of polymer (b) and 485 µg of cilostazol.

Subsequently, cilostazol and polymer (b) were mixed together at a ratio of 1:19 (mass ratio), and dissolved in methylene chloride, to provide a solution. By ultrasonic spray coating, this solution was applied to the first layer, to form a second layer composed of 285 µg of polymer (b) and 15 µg of cilostazol, to obtain a stent of Example 5.

EXAMPLE 6

A cobalt-chromium alloy was used as the stent skeleton member 2. Cilostazol and polymer (b) were mixed together at a ratio of 3:2, and dissolved in methylene chloride, to provide a solution. By ultrasonic spray coating, this solution was applied to the base material cobalt-chromium alloy, to form a first layer composed of 313 µg of polymer (b) and 470 µg of cilostazol.

Subsequently, cilostazol and polymer (c) were mixed together at a ratio of 1:9 (mass ratio), and dissolved in methylene chloride, to provide a solution. By ultrasonic spray coating, this solution was applied to the first layer, to form a second layer composed of 270 µg of polymer (c) and 30 µg of cilostazol, to obtain a stent of Example 6.

EXAMPLE 7

A cobalt-chromium alloy was used as the stent skeleton member 2. Cilostazol and polymer (b) were mixed together at a ratio of 3:2, and dissolved in methylene chloride, to provide a solution. By ultrasonic spray coating, this solution was applied to the base material cobalt-chromium alloy, to form a first layer composed of 490 µg of polymer (b) and 735 µg of cilostazol.

Subsequently, cilostazol and polymer (b) were mixed together at a ratio of 1:19 (mass ratio), and dissolved in methylene chloride, to provide a solution. By ultrasonic spray coating, this solution was applied to the first layer, to form a second layer composed of 285 µg of polymer (b) and 15 µg of cilostazol, to obtain a stent of Example 7.

EXAMPLE 8

Using the same method as the method described in Example 4 except that a first layer composed of 180 µg of polymer (b) and 270 µg of cilostazol was formed, a stent of Example 8 was obtained.

EXAMPLE 9

Using the same method as the method described in Example 4 except that a first layer composed of 247 µg of polymer (b) and 370 µg of cilostazol was formed, a stent of Example 9 was obtained.

Cilostazol Elution Test (In Vitro)
1. Method of Cilostazol Elution Test

Using an elution tester 400-DS (Apparatus 7), and using 10 mL of a phosphate-buffered sodium chloride solution containing 0.25% by mass sodium lauryl sulfate as a test liquid, a test was carried out at an elution test liquid temperature of 37° C. with Dip Speed 10.

Sampling was carried out 0.5, 1, 3, 6, 9, 12, 18, and 24 hours later. The whole amount of the test liquid was replaced at each collection time.

2. Measurement of Elution Rate of Cilostazol (HPLC Measurement)

Under the following conditions, HPLC measurement was carried out for 10 µL of each sample solution or a standard solution. From the peak area values At and As of cilostazol, the elution rate was calculated.

The elution rate was calculated using the following equation.

$$[Q\,hr(\%)] = M_S \times \frac{\sum_{i=P}^{Q} A_T i}{A_S} \times \frac{1}{C} \times A$$

Q: Elution rate (% by mass) for the indicated amount of cilostazol at hour Q
$M_S$: Weighed amount of standard sample of cilostazol (mg)
$A_T$: Peak area of cilostazol sampled at hour i
$A_S$: Peak area of standard solution
C: Indicated amount of cilostazol per stent (≈loaded amount of cilostazol)
A: Constant (0.5)
$\sum_{i=P}^{Q} A_T{}^i$: Sum of the peak area of cilostazol from hour p to hour Q As the indicated amount of cilostazol per stent (C), the amount of loaded cilostazol calculated from the coating mass was used.

Measurement Conditions
Detector: ultraviolet absorptiometer (measurement wavelength: 254 nm)
Column: stainless-steel tube of 4.6 mm (inner diameter)× 150 mm (length), packed with 5-µm octadecylsilyl-modified silica gel for liquid chromatography
Column temperature: constant temperature near 25° C.
Mobile phase: water/acetonitrile/methanol mixed liquid (10:7:3, v/v/v)
Flow rate: adjusted such that the retention time of cilostazol was about 9 minutes
Cilostazol Concentration in Arterial Tissue after Implantation in Rabbit Iliac Artery, and Residual Amount of Cilostazol on Stent (In Vivo)

In a rabbit iliac artery, each of the stents of Examples and Comparative Examples was implanted. The implantation was carried out as follows.

First, the neck of a rabbit is incised to expose the right carotid artery, and an introducer is placed therein. A balloon catheter guide wire is inserted from the introducer, and moved to the distal portion of the treatment site of the iliac artery under X-ray fluoroscopy. Thereafter, an angiographic catheter is inserted along the guide wire, and angiography is carried out for the treatment site of the iliac artery. After the completion of the angiography of the treatment site, a sample balloon catheter is inserted, along the balloon catheter guide wire, to the treatment site under X-ray fluoroscopy. After confirming that the sample stent (standard diameter: 2.75-mm stent diameter at an inflation pressure of 9 atm) is placed in the treatment site of the iliac artery (expected blood vessel diameter, 2.5 mm), the balloon is kept in an inflated state at 14 atm (hyperinflation; expected stent diameter, 3.0 mm; 20% by mass hyperinflation) using an indeflator for 20 seconds each time. After confirming expansion of the stent, the balloon is deflated, and the indeflator is removed, followed by pulling out the balloon catheter along the balloon catheter guide wire. The left and right iliac arteries are treated by the same method.

Subsequently, the angiographic catheter is moved along the balloon catheter guide wire to a position before the treatment site, and angiography is carried out using a diluted contrast agent. After the left and right iliac arteries are treated by the same method, the angiographic catheter is pulled out. Finally, the blood vessel at the sheath insertion site is ligated, and the skin and the muscle layer are sutured. By the above process, the stent is placed in the iliac blood vessel of the rabbit.

Ninety days after the implantation, the cilostazol concentration and the residual stent amount in the arterial tissue at the implantation site of each stent were analyzed.

For pretreatment, the arterial tissue at the implantation site of each stent was separated from the stent. From each sample separated, an organic layer was obtained by liquid-liquid extraction, and then the organic layer was dried to provide a sample. The obtained sample was subjected to LC/MS/MS using the electrospray ionization method, to quantify cilostazol. The cilostazol concentration in the arterial tissue (µg cilostazol in 1 g of the tissue; µg/g tissue) and the residual amount of cilostazol (the residual ratio (%) of cilostazol on the stent) were calculated.

Cilostazol Concentration in Arterial Tissue after Implantation in Pig Iliac Artery, and Residual Amount of Cilostazol on Stent (In Vivo)

The cilostazol concentration in an arterial tissue after implantation in a pig iliac artery, and the residual amount of cilostazol, were evaluated using the same method as the method carried out for the rabbit, to analyze the cilostazol concentration in the arterial, tissue (µg cilostazol in 1 g of the tissue; µg/g tissue) and the residual amount of cilostazol (the residual ratio (%) of cilostazol on the stent) in a pig.

TABLE 2

|  |  | Example | | | Comparative Example | | |
| --- | --- | --- | --- | --- | --- | --- | --- |
|  |  | 1 | 2 | 3 | 1 | 2 | 3 |
| First layer | CLZ/polymer mass ratio<br>CLZ: μg<br>Polymer: μg | CLZ/polymer = 100/0<br>CLZ: 400<br>Polymer: 0 | CLZ/polymer = 100/0<br>CLZ: 400<br>Polymer: 0 | CLZ/polymer = 100/0<br>CLZ: 400<br>Polymer: 0 | CLZ/polymer = 100/0<br>CLZ: 400<br>Polymer: 0 | CLZ/polymer = 100/0<br>CLZ: 400<br>Polymer: 0 | CLZ/polymer = 100/0<br>CLZ: 400<br>Polymer: 0 |
| Second layer | CLZ/polymer mass ratio<br>CLZ: μg<br>Polymer: μg | CLZ/polymer (a) = 1/9<br>CLZ: 60<br>Polymer (a): 540 | CLZ/polymer (b) = 1/9<br>CLZ: 60<br>Polymer (b): 540 | CLZ/polymer (c) = 1/9<br>CLZ: 60<br>Polymer (c): 540 | CLZ/polymer (d) = 1/9<br>CLZ: 60<br>Polymer (d): 540 | CLZ/polymer (e) = 1/9<br>CLZ: 60<br>Polymer (e): 540 | CLZ/polymer (f) = 1/9<br>CLZ: 60<br>Polymer (f): 540 |
| Total | CLZ: μg | 500 | 500 | 500 | 500 | 500 | 500 |
| CLZ elution rate (%) | 24 hours | 1.7 | 3.2 | 1.1 | 51.7 | 17.3 | 39.6 |

TABLE 3

|  |  | Example | | | |
| --- | --- | --- | --- | --- | --- |
|  |  | 4 | 5 | 6 | 7 |
| First layer | CLZ/polymer mass ratio<br>CLZ: μg<br>Polymer: μg | CLZ/polymer (b) = 3/2<br>CLZ: 470<br>Polymer: 213 | CLZ/polymer (b) = 3/2<br>CLZ: 485<br>Polymer: 323 | CLZ/polymer (b) = 3/2<br>CLZ: 470<br>Polymer: 313 | CLZ/polymer (b) = 3/2<br>CLZ: 735<br>Polymer: 490 |
| Second layer | CLZ/polymer mass ratio<br>CLZ: μg<br>Polymer: μg | CLZ/polymer (b) = 1/9<br>CLZ: 30<br>Polymer (b): 270 | CLZ/polymer (b) = 1/19<br>CLZ: 15<br>Polymer (b): 285 | CLZ/polymer (c) = 1/9<br>CLZ: 30<br>Polymer (c): 270 | CLZ/polymer (b) = 1/19<br>CLZ: 15<br>Polymer (b): 285 |
| Total | CLZ: μg | 500 | 500 | 500 | 750 |
| Rabbit CLZ residual ratio (%) | 1 month later<br>3 months later | 100<br>77 | 96<br>89 | 88<br>99.8 | 100<br>91 |
| Pig CLZ concentration in tissue[a] | 3 months later<br>6 months later<br>9 months later | 87<br>57<br>11 | Not measured | Not measured | Not measured |
| Pig CLZ residual ratio (%) | 3 months later<br>6 months later<br>9 months later | 70<br>38<br>2 | Not measured | Not measured | Not measured |
| CLZ elution rate (%) | 24 hours<br>96 hours<br>15 days | 1.6<br>4.3<br>13.2 | Not measured | Not measured | Not measured |

[a] Cilostazol (μg) in 1 g of tissue. Unit: μg/g tissue.

TABLE 4

|  |  | Example | |
| --- | --- | --- | --- |
|  |  | 8 | 9 |
| First layer | CLZ/polymer mass ratio<br>CLZ: μg<br>Polymer: μg | CLZ/polymer (b) = 3/2<br>CLZ: 270<br>Polymer: 180 | CLZ/polymer (b) = 3/2<br>CLZ: 370<br>Polymer: 247 |
| Second layer | CLZ/polymer mass ratio<br>CLZ: μg<br>Polymer: μg | CLZ/polymer (b) = 1/9<br>CLZ: 30<br>Polymer (b): 270 | CLZ/polymer (b) = 1/9<br>CLZ: 30<br>Polymer (c): 270 |
| Total | CLZ: μg | 300 | 400 |
| Pig CLZ concentration in tissue[a] | 3 months later<br>6 months later | 84<br>46 | 78<br>36 |
| Pig CLZ residual ratio (%) | 3 months later<br>6 months later | 66<br>23 | 60<br>14 |
| CLZ elution rate (%) | 24 hours<br>96 hours | 1.7<br>3.8 | 2.7<br>5.6 |

[a] Cilostazol (μg) in 1 g of tissue. Unit: μg/g tissue.

Each of the stents of Examples 1 to 9 comprises a stent skeleton; and a deposition layer containing a plurality of layers deposited on the stent skeleton; each layer of the deposition layer comprising crystalline cilostazol, at least one of the plurality of layers comprising a bioabsorbable polymer, wherein elution of not more than 5% by mass of the crystalline cilostazol occurs by 24 hours after the stent is brought into contact in vitro with an elution medium, at 37° C., of a phosphate-buffered sodium chloride solution containing 0.25% by mass of sodium lauryl sulfate.

Further, each of the stents of Examples 1 to 9 comprises a stent skeleton; and a deposition layer containing a plurality of layers deposited on the stent skeleton; each layer of the deposition layer comprising crystalline cilostazol, at least one of the plurality of layers comprising a bioabsorbable polymer, wherein elution of not more than 20% by mass of the crystalline cilostazol occurs by 15 days after the stent is brought into contact in vitro with an elution medium, at 37° C., of a phosphate-buffered sodium chloride solution containing 0.25% by mass of sodium lauryl sulfate.

Thus, the stents of Examples 1 to 9 are capable of sustained release of cilostazol for more than three months.

Needless to say, the plurality of layers applicable are not limited to two layers, and may be not less than three layers.

In contrast, in each of the stents of Comparative Examples 1 to 3, elution of more than 5% by mass of the crystalline cilostazol occurs by 24 hours after the stent is brought into contact in vitro with an elution medium, at 37° C., of a phosphate-buffered sodium chloride solution containing 0.25% by mass sodium lauryl sulfate.

Thus, the stents of Comparative Examples 1 to 3 are incapable of sustained release of cilostazol for more than three months.

INDUSTRIAL APPLICABILITY

A drug-placing stent of an embodiment of the present invention is capable of allowing elution of not more than 5% by mass of crystalline cilostazol by 24 hours in a test on the elution rate in vitro. Alternatively or additionally, a drug-placing stent of an embodiment of the present invention is capable of allowing elution of not more than 20% by mass of crystalline cilostazol by 15 days in a test on the elution rate in vitro. Thus, the drug-placing stents of the embodiments of the present invention are capable of allowing elution of crystalline cilostazol for a longer period, and can be more suitably used for peripheral blood vessels.

RELATED APPLICATIONS

The present application claims the priority under Article 4 of the Paris Convention based on the application of Application No. 2019-127529 filed in Japan on Jul. 9, 2019. The content of this priority application is incorporated in the present description by reference.

DESCRIPTION OF SYMBOLS

1. Stent
2. Stent skeleton member
3. Deposition layer
4. Ultrasonic spray coating device
5. Ultrasonic spray nozzle
6. Pipe

The invention claimed is:

1. A stent comprising:
a stent skeleton; and
a deposition layer containing a plurality of layers deposited on the stent skeleton;
each layer of the deposition layer comprising crystalline cilostazol,
at least one of the plurality of layers comprising a bioabsorbable polymer,
wherein the deposition layer has at least a first layer and a second layer; the content of cilostazol in the first layer, which is closer to the stent, is higher than the content of cilostazol in the second layer, which is more distant from the stent; and both layers comprise a bioabsorbable polymer,
wherein elution of not more than 5% by mass of the crystalline cilostazol occurs by 24 hours after the stent is brought into contact in vitro at 37° C. with an elution medium of a phosphate-buffered sodium chloride solution containing 0.25% by mass of sodium lauryl sulfate, and
wherein a content of the crystalline cilostazol in the first layer is 55% by mass to 100% by mass.

2. A stent comprising:
a stent skeleton; and
a deposition layer containing a plurality of layers deposited on the stent skeleton;
each layer of the deposition layer comprising crystalline cilostazol,
at least one of the plurality of layers comprising a bioabsorbable polymer,
wherein the deposition layer has at least a first layer and a second layer; the content of cilostazol in the first layer, which is closer to the stent, is higher than the content of cilostazol in the second layer, which is more distant from the stent; and both layers comprise a bioabsorbable polymer,
wherein elution of not more than 20% by mass of the crystalline cilostazol occurs by 15 days after the stent is brought into contact in vitro at 37° C. with an elution medium of a phosphate-buffered sodium chloride solution containing 0.25% by mass of sodium lauryl sulfate, and
wherein a content of the crystalline cilostazol in the first layer is 55% by mass to 100% by mass.

3. The stent according to claim 1, wherein the bioabsorbable polymer comprises not less than 90% by mass of polylactic acid.

4. The stent according to claim 1, wherein the bioabsorbable polymer comprises L-lactide and DL-lactide at a mass ratio of 6:4 to 8:2, and has a viscosity of 1.8 to 4.5 dL/g.

5. The stent according to claim 1, wherein the bioabsorbable polymer comprises not less than 90% by mass of L-lactide, and has a viscosity of 0.6 to 1.4 dL/g.

6. The stent according to claim 1, to be used for a peripheral blood vessel.

7. The stent according to claim 2, wherein the bioabsorbable polymer comprises not less than 90% by mass of polylactic acid.

8. The stent according to claim 2, wherein the bioabsorbable polymer comprises L-lactide and DL-lactide at a mass ratio of 6:4 to 8:2, and has a viscosity of 1.8 to 4.5 dL/g.

9. The stent according to claim 2, wherein the bioabsorbable polymer comprises not less than 90% by mass of L-lactide, and has a viscosity of 0.6 to 1.4 dL/g.

10. The stent according to claim 2, to be used for a peripheral blood vessel.

11. The stent according to claim 1, wherein an outer and exposed layer is bioabsorbable.

12. The stent according to claim 11, wherein the first layer comprises 300 μg to 750 μg of cilostazol drug, and greater than 0 μg to 500 μg of the bioabsorbable polymer, and
the second layer comprises 10 μg to 100 μg of cilostazol, and 180 μg to 540 μg of the bioabsorbable polymer.

13. The stent according to claim 2, wherein an outer and exposed layer is bioabsorbable.

14. The stent according to claim 11, wherein the bioabsorbable polymer comprises L-lactide and DL-lactide at a mass ratio of 6:4 to 8:2, and has a viscosity of 1.8 to 4.5 dL/g,
the first layer comprises 470±47 μg of cilostazol and 313±31 μg of the bioabsorbable polymer, and the second layer comprises 30±3 μg of cilostazol and 270±27 μg of the bioabsorbable polymer.

15. The stent according to claim 13, wherein the bioabsorbable polymer comprises L-lactide and DL-lactide at a mass ratio of 6:4 to 8:2, and has a viscosity of 1.8 to 4.5 dL/g, the first layer comprises 470±47 μg of cilostazol and 313±31 μg of the bioabsorbable polymer, and the second layer comprises 30±3 μg of cilostazol and 270±27 μg of the bioabsorbable polymer.

16. The stent according to claim 1, wherein the second layer is an outer and exposed layer.

17. The stent according to claim 13, wherein the first layer comprises 300 μg to 750 μg of cilostazol drug, and greater than 0 μg to 500 μg of the bioabsorbable polymer, and the second layer comprises 10 μg to 100 μg of cilostazol, and 180 μg to 540 μg of the bioabsorbable polymer.

18. The stent according to claim 2, wherein the second layer is an outer and exposed layer.

19. The stent according to claim 1, wherein the bioabsorbable polymer comprising L-lactide and DL-lactide at a mass ratio of 6:4 to 8:2, and having a viscosity of 1.8 to 4.5 dL/g, the first layer comprising 470±47 μg of cilostazol and 313±31 μg of the bioabsorbable polymer, the second layer comprising 30±3 μg of cilostazol and 270±27 μg of the bioabsorbable polymer.

20. The stent according to claim 2, wherein the bioabsorbable polymer comprising L-lactide and DL-lactide at a mass ratio of 6:4 to 8:2, and having a viscosity of 1.8 to 4.5 dL/g, the first layer comprising 470±47 μg of cilostazol and 313±31 μg of the bioabsorbable polymer, the second layer comprising 30±3 μg of cilostazol and 270±27 μg of the bioabsorbable polymer.

* * * * *